United States Patent [19]

von Alfthan

[11] 3,982,126
[45] Sept. 21, 1976

[54] METHOD AND DEVICE FOR DETERMINING PARTICLE SIZE CATEGORIES OF PARTICLES DISPERSED IN A LIQUID

[75] Inventor: Georg Christian von Alfthan, Helsinki, Finland

[73] Assignee: Outokumpu Oy, Helsinki, Finland

[22] Filed: Mar. 5, 1974

[21] Appl. No.: 448,383

[52] U.S. Cl. ............................. 250/272; 250/273; 356/102
[51] Int. Cl.² ........................................ G01N 23/20
[58] Field of Search ........... 250/272, 273, 362, 363, 250/364; 356/102, 103

[56] References Cited
UNITED STATES PATENTS

| | | | |
|---|---|---|---|
| 3,519,353 | 7/1970 | Franz et al. | 356/102 |
| 3,529,151 | 9/1970 | Carr-Brion | 250/362 |
| 3,621,243 | 11/1971 | Olivier et al. | 356/102 |
| 3,666,943 | 5/1972 | Carr-Brion et al. | 250/272 |
| 3,739,180 | 6/1973 | Carlson | 356/102 |
| 3,749,910 | 7/1973 | Carr-Brion et al. | 250/272 |
| 3,822,095 | 7/1974 | Hirschfeld | 250/273 |

Primary Examiner—Eli Lieberman
Assistant Examiner—B. C. Anderson
Attorney, Agent, or Firm—Charles Mueller

[57] ABSTRACT

In order to determine the size category or categories of particles dispersed in a liquid a sample flow is passed through a flow channel of sufficient length to allow, at a certain point, a stable flow with a predetermined flow velocity distribution over the channel cross section, such velocity distribution also causing a distribution of the particles over the channel cross section according to the particle size, whereupon a measure of the size category is obtained by determining the amounts of particles appearing in different areas of the channel cross section. The method for determining the particle amount in a certain area of the cross section comprises use of an X-ray spectrometer, whereby the size category may be determined for different materials selectively, and at a second point of the channel there may be caused a strong turbulence to assure a uniform distribution of the particles, whereby at this second point there is obtained a corresponding normalizing measure for the equalization of the effects e.g. of density variations in the liquid.

6 Claims, 4 Drawing Figures

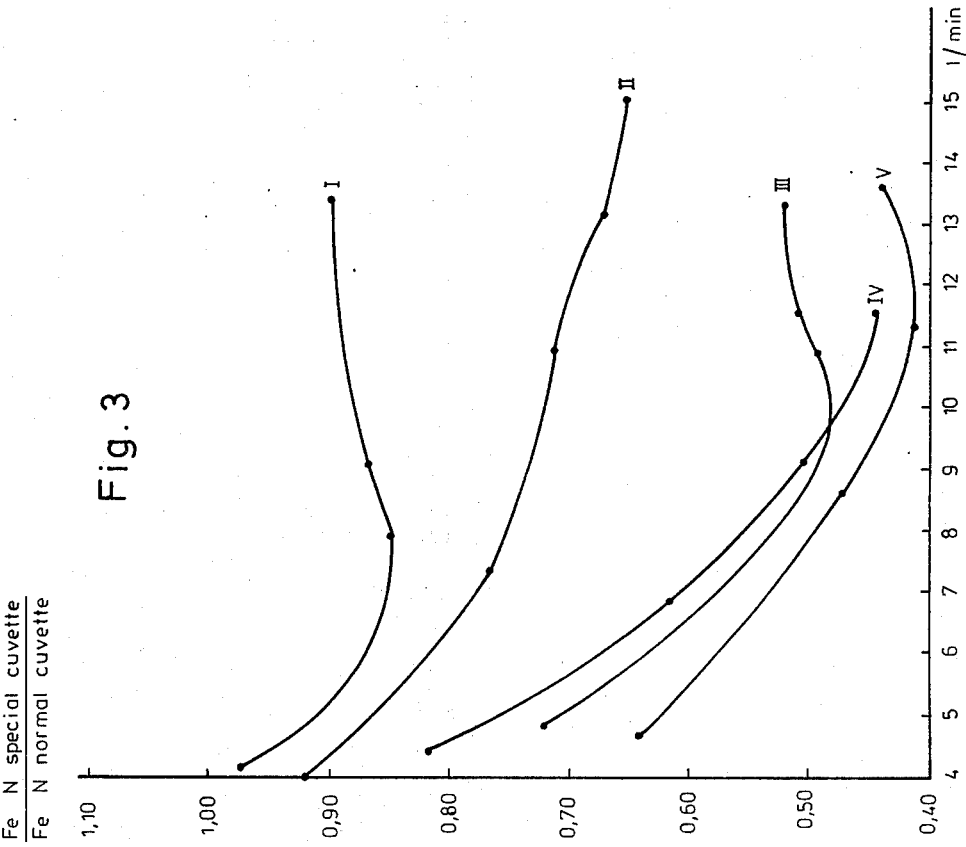

METHOD AND DEVICE FOR DETERMINING PARTICLE SIZE CATEGORIES OF PARTICLES DISPERSED IN A LIQUID

BACKGROUND OF THE INVENTION

1. Field of the Invention

The present invention relates to a method and device for determining the particle size category of particles dispersed in a liquid, also the categories of different materials simultaneously dispersed in the liquid and having different average particle sizes.

2. Description of the Prior Art

Previously known similar methods in which the sample is in the form of a suspension or a solution are usually based on optical observation, the use of ultrasonic methods, or the use of the centrifugal force or gravity affecting the particles in the liquid.

The disadvantage of optical observation is that the multitude of small particles saturates the device and complicates the obtaining of a sufficiently transparent sample.

The disadvantage of ultrasonic devices is their sensitivity to small air bubbles and the complexity of the devices in general.

It is also appropriate to note in this connection that these known optical and ultrasonic methods by no means aim at obtaining a certain areal distribution of the particles, which is the case in the present invention, as described below.

The previously known devices which are based on a centrifugal force or gravity affecting the particles have a disadvantage in that the velocity of the particles is proportional to their density and the second power of their diameter even in an ideal case. Therefore it is difficult, for example, to determine the size of particles with varying density.

Also known is a device in which a suspension flows along a horizontal gutter provided with a measuring rod which moves reciprocally in the vertical direction against a stop at the bottom of the gutter; this rod senses the size of a particle left between the rod and the stop. This device has a substantial disadvantage in that it is capable of measuring the sizes of only the largest particles.

Furthermore, by no known method is it possible to determine separately the sizes of particle categories with different chemical compositions when they are mixed with each other.

SUMMARY OF THE INVENTION

It is an object of the present invention to provide a method and device for relatively precise and rapid particle size analysis, a method and device which are devoid of the disadvantages mentioned above and, in a preferred embodiment, make it possible to carry out a separate analysis concerning a given element even when several particle size categories with different compositions are present in the liquid.

The invention is based on the observation that the particles dispersed in a flowing liquid can be caused to become distributed in a certain manner in relation to the cross section of the flow, depending on the particle size, and the particle size category or categories can be determined by determining the amounts of particles in the different areas of the cross section.

The theory on which the invention is based and which has been developed in connection with the invention is described below briefly to illustrate the invention.

Principally three forces affect a particle in a flowing liquid, namely: (a) gravity, (b) gradient force acting in the direction of the velocity distribution gradient of the liquid flow if the particle moves in relation to the surrounding liquid; a particle moves in the direction in which the velocity difference between the particle surface and the liquid is the greatest, (c) the force caused by the Magnus effect when the particle rotates; even in this case the particle moves in the direction in which the velocity difference between its surface and the surrounding liquid is at its greatest. The movement of a particle is naturally counteracted by friction and its acceleration also by the moment of inertia (cf. Soo, S.L.: Fluid Dynamics of Multiphase Systems, Ginn Blaisdell, 1967).

When the liquid flows in a limited channel, its velocity at the channel wall surface is substantially zero and in the immediate vicinity of the wall there is a laminar boundary layer (cf. FIG. 2). Supposing that gravity effects in the direction of the flow and that the Magnus effect can be ignored, it can be mathematically proven that:

Depending on the viscosity and density of the fluid and other factors, a particle has a critical radius. If its radius is longer than this, the particle ends up in an accelerating movement (in the lateral direction), if it is shorter, the velocity of the particle is slowed down. Above the critical particle size, when the particle is thus accelerated, its velocity grows so high that the assumptions which form the basis of the analysis by calculation no longer apply.

According to this theory, which has been described in a simplified manner here, the laminar (slowly moving) boundary layer of the flow profile becomes devoid of particles with radii longer than the critical one. Deeper in the flow, the flow velocity gradient is smaller and the critical radius respectively longer. There, however, the turbulence of the flow to some extend confuses the situation. The final result is, however, mainly that the particles are distributed in relation to the cross section of the flow so that, according to a growing particle size category, they penetrate even deeper away from the flow channel wall.

This being the case, a spherical particle the diameter of which exceeds a certain limit value determined by the gradient value will not follow the flow but, when it receives even a small initial momentum in a direction perpendicular to the flow, this momentum is accelerated and the particle moves laterally until it meets an obstacle or the gradient decreases. Thus particles are soon redistributed in a manner determined by the flow velocity distribution. Where the flow velocity gradient is high, only the smallest particles remain, the largest ones have been removed.

By investigating the distribution of the amounts of materials in a known flow velocity distribution, quantities which characterize the particle size distribution can be determined. There are several investigation methods. One of the best methods is the excitation of X-ray fluorescence radiation in the particles. In such a case it is possible to investigate separately the distribution of the amount of one given element in the liquid flow.

Following the theory, a device according to the principle described above redistributes the particles in the flow according to a given quantity which is proportional to the first power of their density and to the third power of their diameter. In this case the effect of density is less in this device than in the previous ones. In addition, it is possible to determine separately the quantities which characterize the particle sizes in particle categories with different chemical compositions, by utilizing X-ray fluorescent spectrometry.

In conformity with the theory above, according to the present invention there is provided a method for determining size categories of particles dispersed in a liquid, which comprises bringing a sample of the liquid to flow in a flow channel at stable conditions so, that, at a certain point of the channel there is obtained a predetermined flow velocity distribution over the cross section of the channel and the particles will have had time to distribute over the cross section according to their size and determining the amount of particle materials in different areas of the cross sections by methods previously known.

A preferred device for carrying out this method comprises a channel through which the liquid is caused to flow, a measuring window in the channel wall at a point of the channel preceded by a channel length which ensures a leveling of the liquid flow, and a measuring device known per se, provided in the vicinity of the measuring window to determine the amounts of materials in the various areas of the flow cross section.

BRIEF DESCRIPTION OF THE DRAWINGS

FIG. 3 shows a set of curves to illustrate an experiment made in connection with the invention, and FIG. 4 shows the measured intensity ratio as a function of the mixing ratio of two particle categories distributed in the liquid.

DESCRIPTION OF THE PREFERRED EMBODIMENTS

Figure 1:
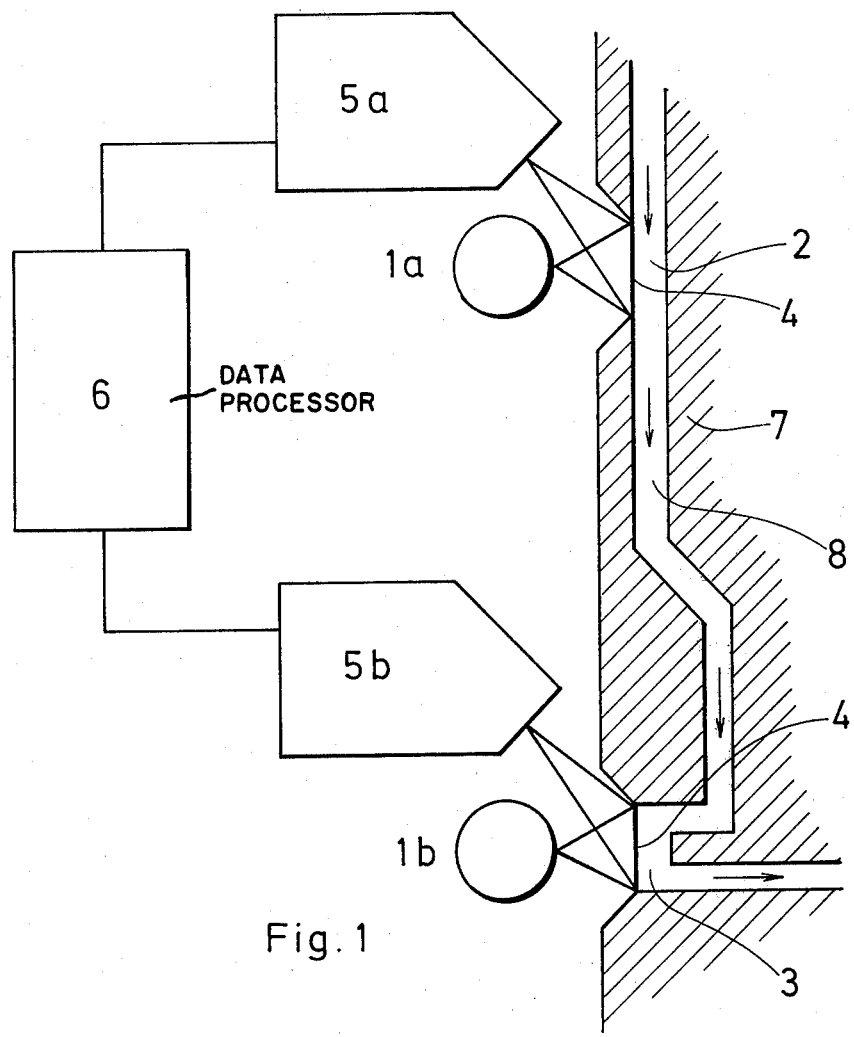
FIG. 1 shows a preferred embodiment of the device according to the invention.

In FIG. 1, a flow channel 8 has been placed in the body 7 of the analyser. At point 2 and within the 20 cm preceding point 2 the cross section of the channel 8 is rectangular. At point 2 the channel is covered with a measuring window 4 made from thin plastic film. A flow as turbulent as possible has been created in part 3. In front of point 3 there is also a thin plastic film 4 permeable to X-rays. The suspension circulates in the channel at a constant flow velocity. Points 2 and 3 are bombarded with X-rays from X-ray sources 1a and 1b. The radiaton emanating from the channel is analyzed by means of X-ray spectrometers 5a and 5b so that the X-ray fluorescence line of a given element or some other parts of the X-ray radiation emanating from points 2 and 3 can be measured. Pulse frequencies corresponding to an intensity of the selected X-ray lines are obtained from both X-ray spectrometers. A quantity calculated by means of these pulse frequencies is obtained electronically in unit 6; this quantity is the measurement. If there is substantially only one heavy element in the suspension, the measurement is the ratio of the intensities obtained directly from measuring points 2, 3. Otherwise, the effects of the different materials must be taken into consideration in a known manner. The measuring device constituting the reference point 3 is called a standard cuvette.

Figure 2:
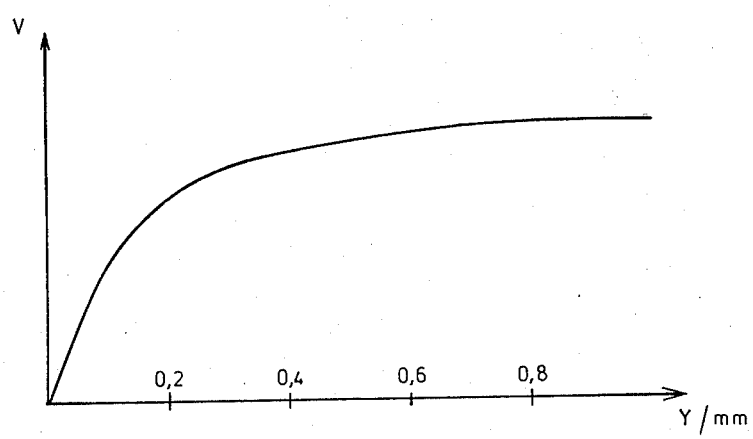
FIG. 2 shows the flow velocity distribution close to the flow channel wall.

The device is meant to be used for solving measuring problems in cases where the particles are in a suspension or a suspension can be made from them. A dispersing agent must be added to the suspension if the particles are in a flocculated state. A sample of the suspension is then pumped at a constant velocity through the flow channel 8. It is important that at point 2 of the channel the particles have become distributed according to their size and the flow velocity distribution. The flow velocity distribution is constant over a sufficiently long distance before point 2 and can be as shown in FIG. 2, for example, in which V indicates the flow velocity and Y the distance from the channel wall. Close to the wall there is a very strong velocity gradient which is approximately constant and which gradually decreases deeper in the flow, where the flow becomes turbulent. Close to the film at point 2 there is a thus formed area with a strong flow gradient. This area has become devoid of coarse particles. Fine particles give a relatively greater X-ray intensity to spectrometer 5a than coarse ones, since some of the fluorescent radiation emitted by coarse particles is absorbed on the surface by a water layer which contains only small particles.

It has been suggested that a reference measurement be used to make it possible to take into consideration the possible suspension density variations. A very turbulent flow has been provided at measurement point 3, and owing to this flow all the large and small particles are fully mixed even in the vicinity of the film 4. Thus, spectrometer 5b receives radiation evenly from both large and small particles.

The quantity calculated by means of the pulse frequencies obtained from the spectrometers 5a and 5b is a good measure for the depth at which the particles on the average move at point 2. This depth, again, is in a certain correlation with the particle size and it can be used as a quantity characterizing the particle size.

In some cases the reference measurement is not necessary; e.g. a constant suspension density or other methods of measuring the suspension density could be used.

When the measuring is carried out in the manner described above, it is possible, for example, to determine the size of iron sulfide crystals almost independently of the suspension material. Often, however, the X-ray fluorescence lines of several elements must be measured, and the quantities characterizing the particle sizes of all the particle types with different chemical compositions are calculated from the intensities on the curves.

The X-ray source 1 can be either an X-ray tube or a radioactive isotope. It is also possible to replace the X-rays with some other radiation, such as $\beta$ or $\alpha$ radiation. The X-ray spectrometers 5 can be either crystal spectrometers, balanced filters, or only X-ray detectors, followed by a pulse height analysis. Different known data processing methods can be used in unit 6. The shape of the flow channel can be varied. The main point is that a controlled flow velocity distribution is obtained at one point and that, on the other hand, the suspension density is known or determined. Furthermore, only one spectrometer and one X-ray source can be used in FIG. 1 so that they are used alternately at points 2 and 3.

A couple of experiments carried out in practice with a device according to FIG. 1 are described below:

EXAMPLE 1

The measuring was carried out at different flow velocities and with five different particle categories which had been sieved by a metallurgical technique and the particle size categories of which were:

| I | <53 | μm | IV | 104–143 | μm |
|---|---|---|---|---|---|
| II | 53–74 | μm | V | >149 | μm |
| III | 74–104 | μm | | | |

The obtained results are given in FIG. 3, in which the ordinate is the ratio between the measurements given by the special cuvette at measurement point 2 and the standard cuvette at reference point 3. It can be observed from the figure that the finer particle categories have given the highest intensity ratios. The general characteristic of the curves is that a rather strong change in the intensity ratio according to the flow velocity takes place at low flow velocities. At higher flow velocities, the decrease in the intensity ratio slows down, and in some cases even a slight increase can be observed, at least within a certain flow velocity range.

Some irregularities can be observed in the measurements, but the curves correspond, however, to those obtained by qualitative theoretical calculation.

The most important difference between the empirical and theoretical numerical values is that considerably higher intensity ratios were obtained empirically than determined theoretically. Obviously for this reason, the intensity ratios of coarse fractions are accumulated approximately at the same level, which is not indicated by the theory. The reasons for the discrepancies between the numerical values in the empirical and theoretical curves may naturally be various. The following "uncertainty factors" are given as examples:

mixing effect of the turbulence;
oversized particles continually appear close to the film for short periods and then withdraw;
reorganization distance given by the cuvette used is very short, 150 mm;
possible effect of the curvature of the cuvette film
effect of the particle shape;
comminution of the particles into smaller ones in the suspension system used.

EXAMPLE 2

By mixing a fine fraction in which the particles were smaller than 53 μm and a coarse fraction in which the particles were larger than 208 μm in different ratios and by measuring the intensity ratios for these different mixtures, the possibilities of characterizing the average particle size by means of this intensity ratio were investigated. Some fine material was also present in the coarse fraction on the basis of previous measurements. The results are given in FIG. 4. The measuring was carried out with five different mixtures. Nevertheless, the last measuring, which was carried out with a mixture which contained coarse particles 100 %, remained uncertain because of certain disturbance factors, for which reason the last part of the curve is indicated with a dotted line. The measured value was, however, about 60 % or slightly lower.

The corresponding theoretical calculations in which formulas of X-rays physics were used agreed to a great extent with the empirically measured curve. It was assumed in the calculations that in the standard cuvette the two fractions were evenly distributed behind the cuvette film and that in the special one the fine fraction was evenly distributed behind the cuvette film and there was no coarse fraction immediately behind the cuvette film but the even distribution of this fraction began at the depth of 0.3 mm.

What is claimed is:

1. A method of determining the mean size of particles dispersed in a liquid which comprises causing a sample of the liquid containing such particles to flow at a steady rate through an elongated straight flow channel having a uniform cross section and maintaining said flow undisturbed for a sufficient distance along said channel for the establishment of a uniform flow velocity distribution over the cross section of the liquid taken perpendicular to the direction of flow at a measuring point to produce a strong flow velocity gradient in the immediate vicinity of a boundary of said channel at said measuring point and thereby obtain a distribution of particles in said vicinity in which relatively smaller ones of said particles tend to be nearer the said boundary than relatively coarser ones of said particles, passing X-ray radiation from an X-ray source into said boundary area of the channel, taking a measurement of the fluorescent radiation from said area to determine the average depth at which the particles move through the channel, said depth being a measure of the particle mean size and taking a second fluorescent radiation measurement at a reference point at which the distribution of said particles is different from the distribution at said first mentioned measurement point.

2. The method of claim 1 in which said reference point measurement includes creating turbulence in the flow before said reference point to produce uniform particle distribution thereat.

3. A device for determining the mean size of particles dispersed in a liquid which comprises a walled channel through which the liquid is caused to flow, said channel having a portion of sufficient length to produce a level and stable state of flow with a uniform flow velocity distribution over the cross section of the liquid taken perpendiculr to the flow direction at a measuring point, a measuring window in the wall of said channel at said measuring point, an X-ray source near said window for passing X-ray radiation into said flow and an X-ray detector, positioned in front of said window to detect fluorescent radiation from the boundary area of the cross section of said flow and thereby determine the average depth at which the particles move through the channel, said depth being a measure of the particle mean size and means for disturbing the flow of said liquid at a reference point to provide uniform size distribution of particles throughout the liquid cross section at said reference point, and a second measuring window and a second X-ray source and detector similar to said first mentioned source and detector and positioned near said second measuring window for determining a reference level related to the total particle density in said boundary area.

4. The device of claim 3 wherein the X-ray detector is a spectrometer.

5. The device according to claim 3 and including data processing means for comparing the relative intensities of fluorescent radiation detected respectively by said first and second X-ray detectors to determine mean particle size.

6. The device of claim 3 wherein the channel is rectangular in cross section and the measuring window consists of a plastic film.

* * * * *

UNITED STATES PATENT AND TRADEMARK OFFICE
CERTIFICATE OF CORRECTION

PATENT NO. : 3,982,126
DATED : September 21, 1976
INVENTOR(S) : GEORG C. VON ALFTHAN It is certified that error appears in the above-identified patent and that said Letters Patent are hereby corrected as shown below:

Column 2, line 40, "extend" should be --extent--

Column 4, line 13, "strong velocity" should be --strong flow velocity--

Column 6, line 40, "perpendiculr" should be --perpendicular--

Signed and Sealed this

Eighteenth Day of January 1977

[SEAL]

Attest:

RUTH C. MASON
Attesting Officer

C. MARSHALL DANN
Commissioner of Patents and Trademarks